United States Patent [19]

Williams

[11] Patent Number: 4,498,482

[45] Date of Patent: Feb. 12, 1985

[54] TRANSVENOUS PACING LEAD HAVING IMPROVED STYLET

[75] Inventor: Terrell M. Williams, Coon Rapids, Minn.

[73] Assignee: Medtronic, Inc., Minneapolis, Minn.

[21] Appl. No.: 518,278

[22] Filed: Jul. 28, 1983

Related U.S. Application Data

[63] Continuation of Ser. No. 296,740, Aug. 27, 1981, abandoned, which is a continuation of Ser. No. 103,249, Dec. 13, 1979, abandoned.

[51] Int. Cl.³ .............................................. A61N 1/04
[52] U.S. Cl. ................................. 128/786; 128/419 P
[58] Field of Search ............. 128/419 P, 772, 784–786

[56] References Cited

U.S. PATENT DOCUMENTS

| | | | |
|---|---|---|---|
| 623,022 | 4/1899 | Johnson | 128/786 |
| 2,221,138 | 11/1940 | Hendrickson | 128/341 |
| 3,630,190 | 12/1971 | Baker | 128/341 |
| 3,683,932 | 8/1972 | Cole | 128/419 P |

FOREIGN PATENT DOCUMENTS

| | | |
|---|---|---|
| 1119158 | 12/1966 | United Kingdom . |
| 1215866 | 7/1968 | United Kingdom . |
| 1277107 | 8/1969 | United Kingdom . |
| 1252170 | 12/1969 | United Kingdom . |
| 1437621 | 6/1973 | United Kingdom . |

OTHER PUBLICATIONS

European Patent Application No. 0 002 904, filed 11.12.78, Application No. 78300788.3 for Dental Probe.

*Primary Examiner*—William E. Kamm
*Attorney, Agent, or Firm*—Reed A. Duthler; Joseph F. Breimayer; John L. Rooney

[57] ABSTRACT

A transvenous pacing lead having a stylet including a longitudinal stylet wire, a handle affixed to the proximal end of the stylet wire, a taper of a predetermined length formed adjacent to or on the distal end of the stylet wire, and a ball affixed to the end of the stylet wire where the ball has a diameter substantially equal to the diameter of the stylet wire. The taper at the distal end of the stylet provides strain relief, least rigidity of the stylet wire and complies with the curvature bends of the transvenous pacing lead. The tapered end of the stylet wire can also be referred to as a soft tip stylet wire.

8 Claims, 5 Drawing Figures

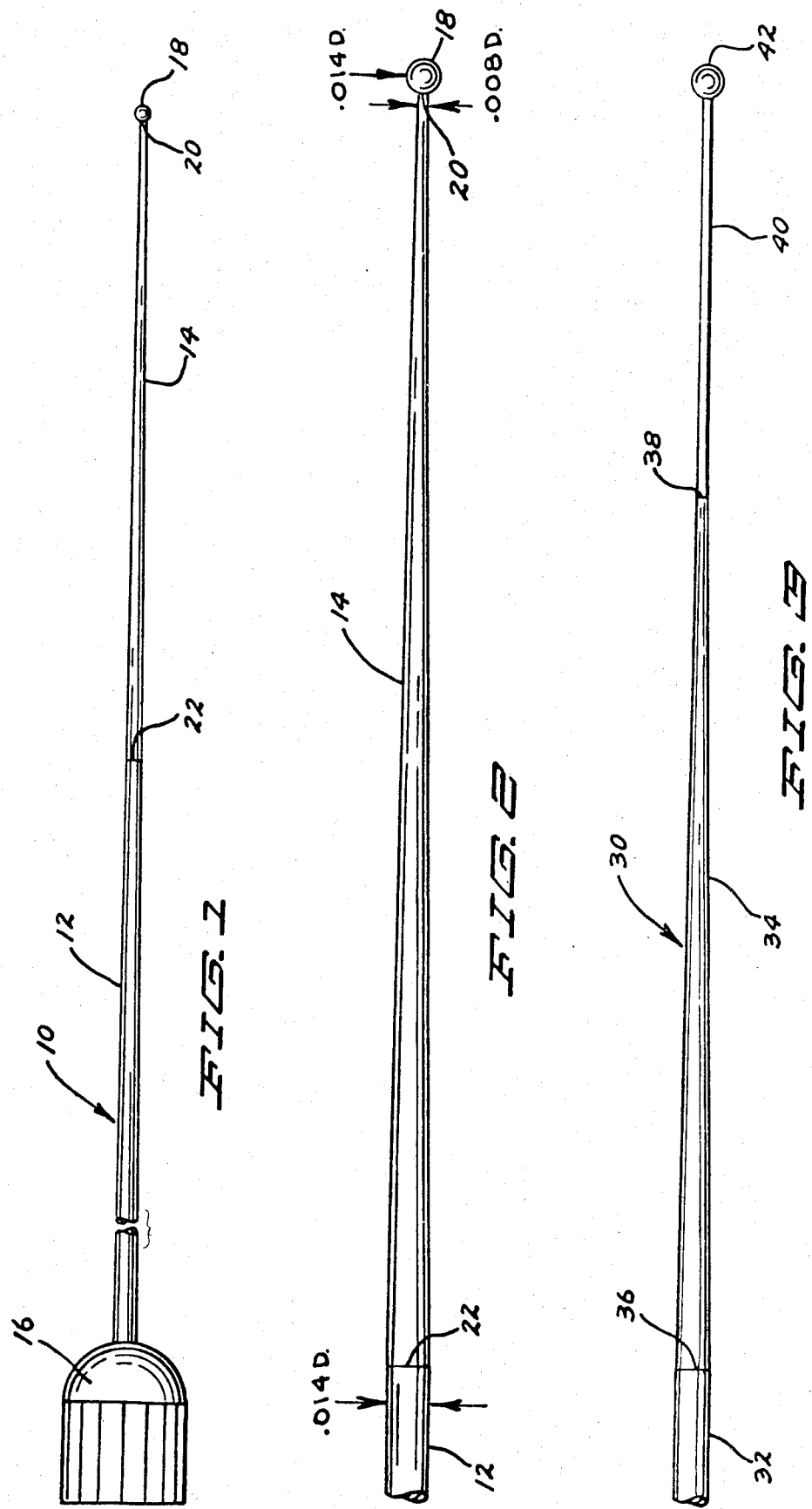

4,498,482

TRANSVENOUS PACING LEAD HAVING IMPROVED STYLET

This application is a continuation of application Ser. No. 296,740, filed Aug. 27, 1981, now abandoned which is a continuation of U.S. Ser. No. 103,249, filed Dec. 13, 1979, now abandoned.

BACKGROUND OF THE INVENTION

1. Field of the Invention

The present invention pertains to a surgical instrument, and more particularly, pertains a transvenous pacing lead with to a stylet having a tapered distal end and a ball affixed to the end of the stylet wire.

2. Description of the Prior Art

Prior art stylets for transvenous pacing lead usually have consisted of a stylet wire with constant diameter along the entire longitudinal length of the stylet wire and including a handle affixed to the proximal end. This type of stylet has two disadvantages: the first being rigidity along the entire longitudinal length of the stylet wire; and the second being that the end of the stylet wire sometimes punctures through the coil end insulation of a transvenous pacing lead. The first disadvantage with a stylet wire of constant diameter is that there is limited flexibility as the entire length of the stylet wire is rigid, especially at the end of the stylet wire. Consequently, the stylet wire sometimes does not comply with the bends and curvatures of a transvenous pacing lead during insertion of the pacing lead. Also, it is sometimes difficult for medical personnel to push a stylet wire through a transvenous pacing lead. The second disadvantage is that the sharp edges of the distal end of the stylet wire sometimes will protrude through a curve or bend in a transvenous pacing lead thereby violating the wire coil and insulation of the lead. Sometimes, the end of the sytlet wire will also puncture the vein or worse yet, puncture heart tissue or heart wall. Also, instead of the stylet complying to a bend in the lead, the leads bend becomes sharper, using present stylets, allowing the stylet tip to perforate the lead.

The stylet of the present invention provides a taper at the distal end of the stylet, thereby providing a soft tip stylet and also includes a ball on the end of the taper providing for easy compliance while being passed through new compliant transvenous pacing lead now on the stylet.

SUMMARY OF THE INVENTION

The present invention is a transvenous pacing lead having a soft tip stylet which complies with curvatures and bends of the transvenous pacing lead and includes a ball at the distal end of the stylet wire which easily passes through the transvenous pacing lead.

According to one embodiment of the present invention, there is provided a stylet including a stylet wire having a handle affixed to a proximal end, a taper at the distal end at or near the distal end of the stylet wire, and a round ball affixed to the distal end of the stylet wire whereby the taper at or near the distal end of the stylet wire provides strain relief and compliance with curvatures and bends while passed through a transvenous pacing lead and the ball at the distal end of the taper of the stylet wire provides for easy pass-through of the distal end of the stylet wire through the transvenous pacing lead.

A significant aspect and feature of the present invention is a taper at or near and adjacent to the distal end of the stylet wire which provides for a soft distal tip end of the stylet wire which conforms to the bends and curves of the transvenous pacing lead.

BRIEF DESCRIPTION OF THE DRAWINGS

Other objects and many of the attendant advantages of this invention will be readily appreciated as the same becomes better understood by reference to the following detailed description when considered in connection with the accompanying drawing in which like reference numerals designate like parts throughout the FIGURES thereof and wherein:

FIG. 1 illustrates a plan view of a stylet, the present invention, where the distal end is shown in an exploded view and the proximal end is broken;

FIG. 2 illustrates an exploded plan view of the distal end of the stylet; and,

FIG. 3 illustrates an exploded plan view of an alternative embodiment of a distal end of an alternative stylet.

DESCRIPTION OF PREFERRRED EMBODIMENT

Figure 4:
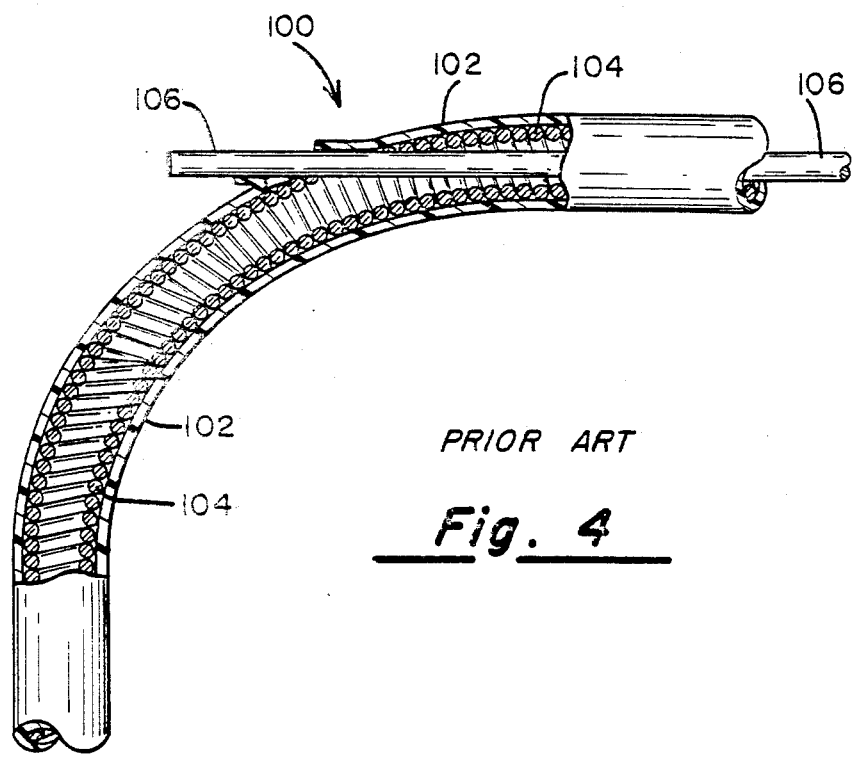
FIG. 4 illustrates a prior art stylet violating the wound coil and protruding through the insulation of a prior art transvenous pacing lead.
Figure 5:
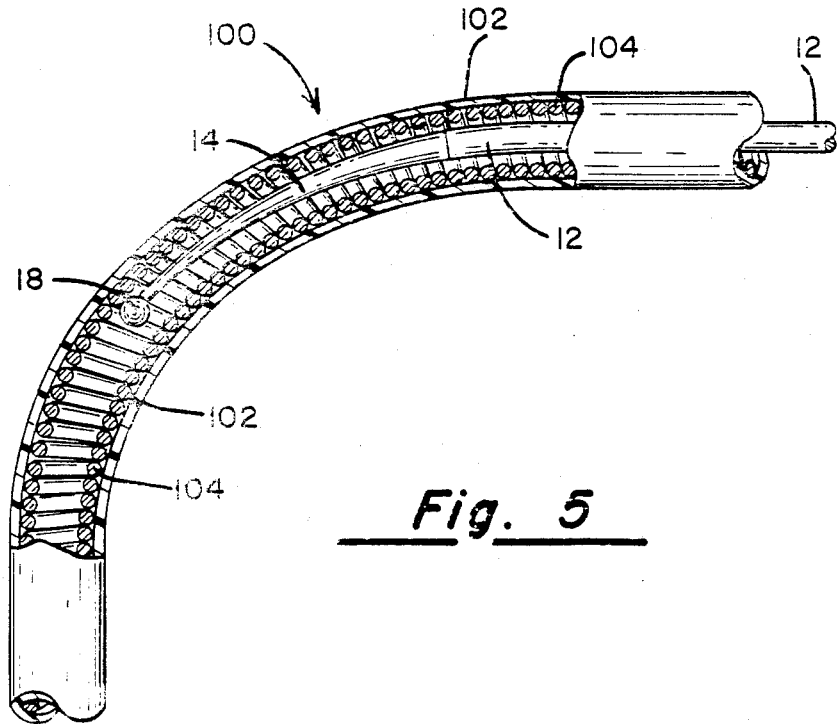
FIG. 5 illustrates the insertion of the improved stylet.

FIG. 1, which illustrates a plan view of a stylet 10, according to the present invention, shows a longitudinal stylet wire 12 having a taper 14 at the distal end and a handle 16 affixed to the proximal end of the stylet wire 12 by structure known in the art. For purposes of clarity in the drawings for illustrating the distal end and proximal end of the stylet wire 12, the stylet wire is broken as illustrated in the figure. Ball 18 is affixed to a distal end 20 of the taper 14 by processes known in the art, such as by welding.

Taper 14 is a gradual taper from junction 22 of the diameter of the wire where the taper begins to the distal end 20 of the stylet wire 12 at which point the ball 18 is secured to the distal end 20. Taper 14 can be formed such as by centerless grinding or a drawn process by way of example and for purposes of illustration only. The length of the taper 14 is predetermined by a number of factors, such as the diameter of the stylet wire, the spring constant of the stylet wire, the particular application of the stylet for use in a transvenous pacing lead to a heart appendage, and other considerations as dictated by the medical factors. The length of the taper 14 can vary in the range of a couple inches, such as three or four, to a quarter of an inch over the length of the taper 14. By way of example and for purposes of illustration, the taper 14 has been shown to extend over one-half inch of the distal end of the stylet wire 12. The diameter of the ball 18 is considered to be the same diameter as the diameter of the stylet wire, but may range in size to be more or less than the diameter of the stylet wire 12.

FIG. 2, which illustrates an exploded plan view of the distal end of the stylet wire, shows the stylet wire 12 having a diameter of 0.014 inches, a taper from the junction 22 down to the distal end 20 of 0.014 to 0.008 inches, although the 0.008 inches could be in the range of 0.01 to 0.006 or less or, alternatively as great as 0.009 to 0.013 and the diameter of the ball 18 is substantially equal to the diameter of stylet wire 12, 0.014 inches.

PREFERRED MODES OF OPERATION

The stylet 10 of the present invention can be inserted into a transvenous pacing lead 100 before the transvenous pacing lead 100 is passed through a vein, or in the alternative, stylet 12 can be inserted into the transvenous pacing lead 100 on initial passing of the transvenous pacing lead 100 through a vein or after the distal end of the lead 100 has been placed within the body. The ball 18 provides smooth insertion of the stylet 12 within a transvenous pacing lead 100 without the concern of the distal end of the stylet wire 12 violating the wound coil 104 of the transvenous pacing lead 100 or protruding through the insulation 102 of the transvenous pacing lead 100 as contrasted with prior art stylet 106 as shown in FIG. 4. The distal end of the stylet 12, especially over the length of the taper 14, provides a soft tip which complies with the curvature and bends of the transvenous pacing lead, allowing for easy insertion and control around the curves and bends of the lead.

ALTERNATIVE EMBODIMENT

FIG. 3, which illustrates an exploded plan view of a distal end for an alternative embodiment of a stylet 30, includes a stylet wire 32 having a constant diameter, the proximal end which connects to a stylet handle as previously described for FIGS. 1 and 2 and not illustrated for purposes of clarity in the drawing and having a taper 34 running from the function 36 of the constant diameter of the stylet wire 32 and the taper 34 to a junction 38 of the end of the taper 34 of the stylet wire 32 and a wire 40 of constant diameter. A ball 42 of a diameter substantially equal to the diameter of the stylet wire 32 affixes to the distal end of the constant diameter wire 40. As previously described and by way of example and for purposes of illustration only, the diameter of the stylet wire 32 can be 0.014 inches, the taper can occur three-quarters of the length of the stylet wire from the junction 36, such as from 0.014 inches to 0.008 inches, to the ball 42 and remaining wire 40 can be of constant diameter of 0.008 inches by way of example and for purposes of illustration only while the constant diameter wire 40 can be in the last one-quarter of the length of the distal end from junction 36 to ball 42. The numerical diameters and length are by way of example and for purposes of illustration only in illustrating an operative alternative embodiment of the present invention, can be varied depending upon the particular medical application, and is not to be construed as limiting of the present invention.

Various modifications can be made to the stylet of the present invention without departing from the apparent scope of the present invention.

Having thus described the present invention, there is claimed:

1. In a transvenous pacing lead of the type having a wound coil surrounded by insulation and a stylet, removably insertable in said pacing lead, an improvement wherein said stylet is provided with first means for allowing easy control around bends and curves of said transvenous pacing lead, and is provided with second means coupled to said first allowing means for preventing said stylet from violating said wound coil or protruding through said insulation.

2. A transvenous pacing lead according to claim 1 wherein said stylet further comprises:
   a stylet wire having a first diameter coupled proximally to said first allowing means; and
   a knob coupled to a proximal end of said stylet wire.

3. A transvenous pacing lead according to claim 2 wherein said first allowing means is a wire being smoothly tapered from said first diameter to a smaller second diameter.

4. A transvenous pacing lead according to claim 3 wherein said first diameter is 0.014 inches.

5. A transvenous pacing lead according to claim 4 wherein said second diameter is 0.008 inches.

6. A transvenous pacing lead according to claim 1, 2, 3, 4, or 5 wherein said second preventing means is a sphere fixedly attached to a distal end of said first allowing means.

7. A transvenous pacing lead according to claim 6 wherein said sphere has a diameter of 0.014 inches.

8. A transvenous pacing lead according to claim 2, 3, 4 or 5 wherein said second preventing means is a sphere fixedly attached to a distal end of said first allowing means wherein said sphere has a third diameter which is equal to said first diameter.

* * * * *